US010258043B2

(12) United States Patent
Nouvel et al.

(10) Patent No.: US 10,258,043 B2
(45) Date of Patent: Apr. 16, 2019

(54) PESTICIDE COMPOSITIONS AND METHODS FOR CONTROLLING INVERTEBRATE PESTS

(71) Applicant: Adama Makhteshim Ltd., Beer Sheva (IL)

(72) Inventors: Larry Mearns Nouvel, Plano, TX (US); Mark Allen Boyd, Seabrook, CT (US)

(73) Assignee: ADAMA MAKHTESHIM LTD., Beer-Sheva (IL)

( * ) Notice: Subject to any disclaimer, the term of this patent is extended or adjusted under 35 U.S.C. 154(b) by 0 days.

(21) Appl. No.: 14/437,670

(22) PCT Filed: Oct. 17, 2013

(86) PCT No.: PCT/IL2013/050837
§ 371 (c)(1),
(2) Date: Apr. 22, 2015

(87) PCT Pub. No.: WO2014/064681
PCT Pub. Date: May 1, 2014

(65) Prior Publication Data
US 2015/0296789 A1 Oct. 22, 2015

Related U.S. Application Data

(60) Provisional application No. 61/718,960, filed on Oct. 26, 2012, provisional application No. 61/788,385, filed on Mar. 15, 2013.

(51) Int. Cl.
*A01N 47/34* (2006.01)
*A01N 43/40* (2006.01)

(52) U.S. Cl.
CPC ............ *A01N 47/34* (2013.01); *A01N 43/40* (2013.01)

(58) Field of Classification Search
CPC .................. A01N 47/34; A01N 43/40
See application file for complete search history.

(56) References Cited

U.S. PATENT DOCUMENTS

| 6,093,415 A * | 7/2000 | Karr .................. A01N 47/34 424/405 |
| 2003/0032669 A1* | 2/2003 | Verbruggen .......... A01N 47/34 514/479 |
| 2004/0024026 A1 | 2/2004 | Morita et al. |
| 2005/0137244 A1* | 6/2005 | Boeckh ................ A01N 43/56 514/406 |

FOREIGN PATENT DOCUMENTS

| JP | 2009161471 A | 7/2009 | |
| WO | WO 9323998 A1 * | 12/1993 | ............ A01M 1/026 |
| WO | 9533380 A1 | 12/1995 | |
| WO | 9834481 A1 | 8/1998 | |
| WO | 0165942 A1 | 9/2001 | |
| WO | 2005087002 A2 | 9/2005 | |
| WO | 2006048868 A2 | 5/2006 | |
| WO | 2010076782 A2 | 7/2010 | |
| WO | 2012017428 A2 | 2/2012 | |
| WO | 2014072970 A1 | 5/2014 | |

OTHER PUBLICATIONS

Ameen et al. Journal of Economic Entomology, (2005), 98(3), p. 899-905.*
Smith et al. Proceedings of the 4th International Conference on Urban Pests, (2002) p. 345-352.*
PCT Third Party Observation; International Application No. PCT/IL2013/050837; International Filing Date Oct. 17, 2013; 2 pages.
International Search Report and Written Opinion of the International Searching Authority for PCT/IL2013/050837 dated Feb. 24, 2014, 11 pages.
Ross, M.H., et al., "Effects on German cockroach nymphs of contact exposure to IGRs singly and in combination", Entomol. Exp. Appl., vol. 61, No. 2, pp. 117-122, (1991) XP002719677.
Meola et al.; "Physiological Effects of the Juvenoid Pyriproxyfen on Adults, Eggs, and Larvae of the Cat Flea"; Proceedings of the First International Conference on Urban Pests; K.B. Wildey and Wm. H. Robinson (editors); 1993; pp. 221-228.

* cited by examiner

*Primary Examiner* — Yong L Chu
(74) *Attorney, Agent, or Firm* — Gary J. Gershik; Cooper & Dunham LLP

(57) ABSTRACT

The present invention discloses a pesticide composition comprising a juvenoid, such as pyriproxyfen or hydroprene, and a chitin synthesis inhibitor, such as novaluron. The composition containing the combined actives provides an increased efficacy not exhibited by either active when used alone.

20 Claims, No Drawings

PESTICIDE COMPOSITIONS AND METHODS FOR CONTROLLING INVERTEBRATE PESTS

This application is a national stage application PCT/IL2013/050837, filed Oct. 17, 2013, which claims priority to U.S. Provisional Application Ser. No. 61/788,385 filed Mar. 15, 2013 and U.S. Provisional Application Ser. No. 61/718,960 filed Oct. 26, 2012, which are hereby incorporated by reference in their entirety.

FIELD OF INVENTION

The present invention relates to a pesticide composition comprising active pesticides comprising a juvenoid selected from the group consisting of epofenonane, fenoxycarb, hydroprene, kinoprene, methoprene, pyriproxyfen, triprene, and combinations thereof; and, a chitin synthesis inhibitor selected from the group consisting of bistrifluron, buprofezin, chlorfluazuron, cyromazine, diflubenzuron, flufenoxuron, flucycloxuron, hexaflumuron, lufenuron, novaluron, noviflumuron, penfluron, teflubenzuron, triflumuron, and combinations thereof, which composition provides quicker and more effective control against invertebrate pests.

The present invention also relates to a method for controlling invertebrate pests by applying a pesticidal concentrate comprising the pesticide composition dispersed in an aqueous medium to an area where pest control is needed.

DESCRIPTION OF RELATED ART

Flea, cockroach, beetle, and other crawling insect infestation in human dwelling areas and business areas is not only a nuisance, but can also be the cause of public health concerns, since such insects have been known to carry certain diseases. For example, cockroaches are among the oldest living forms of life on our planet, are remarkable survivors, can go weeks without food or water and have adapted to conditions in nearly every environment imaginable. Common American cockroaches, such as the Oriental, the brown-banded, the smokey brown, and the most widespread, the German cockroach, are known to transmit at least 13 human diseases, including typhoid, dysentery, hepatitis, allergies, and leprosy.

There are many known pesticides used to combat fleas, cockroaches, beetles and other crawling insects and, for the most part, these known insecticides are effective at killing live adult insects present in dwelling or business areas when properly used. However, when just the live adult insects are targeted, they are still capable of reproducing or laying eggs before they die and therefore such pesticide regimes do not effectively prevent further infestation and more pesticide is required to be applied, which may negatively affect the non-target inhabitants of residential or commercial areas.

Insect growth regulators (or IGRs) are generally compounds that are capable of disrupting the growth and development of pest species, so that the pest cannot mature and reproduce, thereby preventing further infestation. IGRs are often described as "biorational" insecticides in that they have a unique mode of action specific to insects that is essentially nontoxic to other animals, including humans. As an insect grows, it undergoes a process called molting where it grows a new exoskeleton under its old one and then sheds the old exoskeleton to allow the new one to swell to a new size and harden. Cockroaches go through approximately 5 molts before becoming reproductive adults, a process called incomplete metamorphosis. This process depends on the intricate and exact interaction of biochemical regulation controlled by glands in the insect brain. If this process is interrupted, normal molting, metamorphosis and reproduction do not occur in those insects, which cause death.

There are two common classes of IGRs, namely juvenile hormone mimics (or juvenoids) and chitin synthesis inhibitors (CSIs). Juvenoids, such as hydroprene, methoprene, kinoprene, triprene, fenoxycarb, and pyriproxyfen, bind to juvenile hormone binding cite receptors and mimic the action of the juvenile hormones, thereby inhibiting embryogenesis, metamorphosis and adult formation. CSIs, such as novaluron, prevent the formation of chitin, a carbohydrate needed to form the insect's exoskeleton. With these inhibitors, an insect grows normally until it molts. The inhibitors prevent the new exoskeleton from forming properly, causing the insect to die. Death may be quick, or may take up to several days or months depending on the insect. CSIs can also kill eggs by disrupting normal embryonic development.

Because IGRs work by interfering with an insect's molting process (which for German cockroaches takes approximately 5 months), using an IGR to control could take months before any relief is observed. Moreover, IGRs (by themselves) are not typically viewed as effective pest control since they do not kill pre-existing pests. Therefore, in order to meet the demands of consumers for immediate relief of pest infestations, IGRs are typically combined with a conventional insecticide (i.e., an adulticide such as a pyrethroid or a phenylpyrazole) in order to provide effective pest control as desired by consumers. Unfortunately, the toxicity of conventional insecticides presents significant risks when used in confined areas and in areas inhabited by animals and humans.

Therefore, given the observed shortcomings of juvenoids and chitin synthesis inhibitors when used alone in the pest control industry to quickly and effectively eradicate pest infestations, as well as the toxicity of an IGR combined with a conventional insecticide to non-target organisms, it would be desirable to provide a pesticide composition comprising only a combination of IGRs (specifically, a juvenoid combined with a chitin synthesis inhibitor) that would quickly and effectively provide multiple opportunities to disrupt the lifecycle (molting, metamorphosis, and reproduction) of pests in order to eradicate an infestation quicker than by using a single IGR by itself. Moreover, a combined IGR pesticide containing a juvenoid and a chitin synthesis inhibitor would eliminate the need to further include a conventional insecticide and thereby diminish the toxicity to non-target organisms.

SUMMARY OF THE INVENTION

It has been unexpectedly found that a pesticide composition comprising active pesticides, wherein the active pesticides comprise a juvenoid selected from the group consisting of epofenonane, fenoxycarb, hydroprene, kinoprene, methoprene, pyriproxyfen, triprene, and combinations thereof; and a chitin synthesis inhibitor selected from the group consisting of bistrifluron, buprofezin, chlorfluazuron, cyromazine, diflubenzuron, flufenoxuron, flucycloxuron, hexaflumuron, lufenuron, novaluron, noviflumuron, penfluron, teflubenzuron, triflumuron, and combinations thereof, provides improved efficacy against invertebrate pests, namely, cockroaches, fleas, and beetles.

The pesticide compositions of the present invention are preferably dispersed in an aqueous medium (e.g., water and/or an organic solvent) thereby forming a pesticide concentrate. It has been found that the application of the novel pesticide concentrate (containing a pesticide composition comprising a combination of a juvenoid and a chitin synthesis inhibitor) to an area infested by insects provides quicker and more effective control of pests than would be experienced following application of a pesticide concentrate containing either IGR by itself.

The present invention generally relates to a pesticide composition comprising active pesticides comprising from about 1% to about 69% by weight of a juvenoid selected from the group consisting of epofenonane, fenoxycarb, hydroprene, kinoprene, methoprene, pyriproxyfen, triprene, and combinations thereof; and, from about 1% to about 69% by weight of a chitin synthesis inhibitor selected from the group consisting of bistrifluron, buprofezin, chlorfluazuron, cyromazine, diflubenzuron, flufenoxuron, flucycloxuron, hexaflumuron, lufenuron, novaluron, noviflumuron, penfluron, teflubenzuron, triflumuron, and combinations thereof, wherein the composition comprises up to 70% by weight of total active pesticide.

Further, the present invention is directed to a pesticide concentrate comprising (1) a pesticide composition comprising active pesticides comprising from about 0.5% and about 69.5% by weight of a juvenoid selected from the group consisting of epofenonane, fenoxycarb, hydroprene, kinoprene, methoprene, pyriproxyfen, triprene, and combinations thereof, and from about 0.5% to about 69.5% by weight of a chitin synthesis inhibitor selected from the group consisting of bistrifluron, buprofezin, chlorfluazuron, cyromazine, diflubenzuron, flufenoxuron, flucycloxuron, hexaflumuron, lufenuron, novaluron, noviflumuron, penfluron, teflubenzuron, triflumuron, and combinations thereof, wherein the composition comprises up to 70% by weight of total active pesticide; and (2) an aqueous medium, such that the pesticide composition is dispersed in the aqueous medium to form the pesticide concentrate comprising from about 0.005% to about 0.5% by weight of the active pesticides.

In addition, the present invention further provides a method of controlling cockroaches and fleas in a confined area, the method comprising applying a pesticide concentrate to a locus where pest control is required, the pesticide concentrate comprising (1) a pesticide composition comprising active pesticides comprising from about 0.5% to about 69.5% by weight of a juvenoid selected from the group consisting of epofenonane, fenoxycarb, hydroprene, kinoprene, methoprene, pyriproxyfen, triprene, and combinations thereof, and from about 0.5% to about 69.5% by weight of a chitin synthesis inhibitor selected from the group consisting of bistrifluron, buprofezin, chlorfluazuron, cyromazine, diflubenzuron, flufenoxuron, flucycloxuron, hexaflumuron, lufenuron, novaluron, noviflumuron, penfluron, teflubenzuron, triflumuron, and combinations thereof, wherein the composition comprises up to 70% by weight of total active pesticide; and (2) an aqueous medium; wherein the pesticide composition is dispersed in the aqueous medium to form the pesticide concentrate comprising from about 0.005% to about 0.5% (w/w) of the active pesticides.

Unless otherwise defined, all technical and scientific terms used herein have the same meaning as is commonly understood by one of skill in the art to which this invention belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

DETAILED DESCRIPTION

The pesticide compositions and concentrates provided herein utilize a combination of a juvenoid and a chitin synthesis inhibitor to treat pest infestations and prevent future infestations in confined areas such as a household residence, hospital, business office, transportation equipment (e.g., automobile, boat, truck, bus, boxcar, etc.), animal quarters, commercial building, or warehouse, as well as open areas, such as crop farms. The compositions and concentrates of the present invention are based in part on the finding that application of the novel pesticide concentrate of the present invention to a locus or area where pest control is desired results in improved control of pests and prevents further infestation.

Generally, the pesticide concentrate comprises (1) a pesticide composition comprising active pesticides comprising from about 0.5% to about 69.5% by weight of a juvenoid selected from the group consisting of epofenonane, fenoxycarb, hydroprene, kinoprene, methoprene, pyriproxyfen, triprene, and combinations thereof; and from about 0.5% to about 69.5% by weight of a chitin synthesis inhibitor selected from the group consisting of bistrifluron, buprofezin, chlorfluazuron, cyromazine, diflubenzuron, flufenoxuron, flucycloxuron, hexaflumuron, lufenuron, novaluron, noviflumuron, penfluron, teflubenzuron, triflumuron, and combinations thereof, wherein the composition comprises up to 70% by weight of total active pesticide; and (2) an aqueous medium; wherein the pesticide composition is dispersed in the aqueous medium to form the pesticide concentrate comprising from about 0.005% to about 0.5% by weight of the active pesticides. All percents provided herein are percent by weight based on the total weight of the composition, unless otherwise noted.

The pesticide composition comprises a combination of IGRs, namely a juvenoid and a chitin synthesis inhibitor, and may optionally include other active pesticides known in the art. Alternatively, the active pesticides may consist only of a juvenoid and a chitin synthesis inhibitor.

The juvenoid is selected from the group consisting of epofenonane, fenoxycarb, hydroprene, kinoprene, methoprene, pyriproxyfen, triprene, and combinations thereof. Juvenoids bind to juvenile hormone binding cite receptors and mimic the action of the juvenile hormones, thereby inhibiting embryogenesis, metamorphosis and adult formation. Juvenile hormone must be absent for a pupa to molt to an adult, so juvenoid treated larvae are unable to successfully develop from pupa to an adult pest, preventing them from reproducing. The amount of juvenoid present in the composition should be equal to from about 0.5% to about 69.5% by weight. Preferably, the composition comprises from about 1% to about 30% by weight of a juvenoid. Even more preferably, the composition comprises from about 1% to about 10% by weight of a juvenoid. In a preferred embodiment, the composition comprises about 1.3% by weight of a juvenoid.

In a preferred embodiment, the juvenoid is pyriproxyfen. Pyriproxyfen is also known as 4-phenoxyphenyl 2-(2-pyridyloxy)propyl ether or 2-[1-(4-phenoxyphenoxyl)propan-2-yloxy]pyridine, and is marketed under the trade name Nylar™. The chemical structure for pyriproxyfen is shown below.

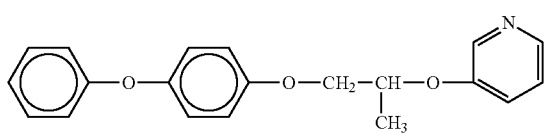

It is understood that analogs and associated derivatives of pyriproxyfen (including enantiomers, diastereomers, racemates, or pharmaceutically acceptable salts thereof) are also within the scope of the present invention.

In another embodiment, the juvenoid is hydroprene. The chemical structure for hydroprene is shown below.

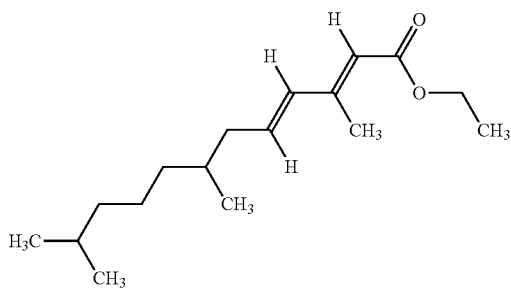 [SMILES: CCOC(=O)/C=C(C)/C=C/CC(C)CCCC(C)C]

It is understood that analogs and associated derivatives of hydroprene (including enantiomers, diastereomers, racemates, or pharmaceutically acceptable salts thereof) are also within the scope of the present invention.

The chitin synthesis inhibitor is selected from the group consisting of bistrifluron, buprofezin, chlorfluazuron, cyromazine, diflubenzuron, flufenoxuron, flucycloxuron, hexaflumuron, lufenuron, novaluron, noviflumuron, penfluron, teflubenzuron, triflumuron, and combinations thereof. Chitin synthesis inhibitors achieve their efficacy by preventing the formation of chitin, a carbohydrate needed to form the insect's exoskeleton. With these inhibitors, an insect grows normally until it molts. The inhibitors prevent the new exoskeleton from forming properly, causing the insect to die. Death may be quick, or may take up to several days or months depending on the insect. Chitin synthesis inhibitors can also kill eggs by disrupting normal embryonic development. The amount of chitin synthesis inhibitor present in the composition should be equal to from about 0.5% to about 69.5% by weight. Preferably, the composition comprises from about 1% to about 30% by weight of a chitin synthesis inhibitor. Even more preferably, the composition comprises from about 1% to about 10% by weight of a chitin synthesis inhibitor. In a preferred embodiment, the composition comprises about 1.3% by weight of a chitin synthesis inhibitor.

In a preferred embodiment, the chitin synthesis inhibitor is novaluron. Novaluron is also known as (RS)-1-[3-chloro-4-(1,1,2-trifluoro-2-trifluoromethoxyethoxy)phenyl]-3-(2,6-difluorobenzoyl)urea. The chemical structure for novaluron is shown below.

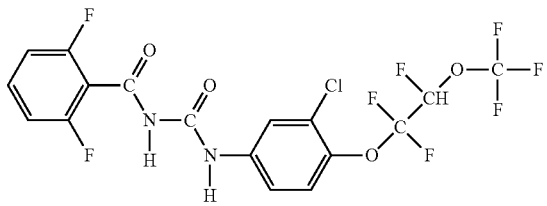 [SMILES: O=C(NC(=O)c1c(F)cccc1F)Nc1ccc(OC(F)(F)C(F)OC(F)(F)F)c(Cl)c1]

It is understood that analogs and associated derivatives of novaluron (including enantiomers, diastereomers, racemates, or pharmaceutically acceptable salts thereof) are also within the scope of the present invention.

A basic pesticide composition used to form the pesticide concentrates of the present invention comprises from about 0.5% to about 69.5% by weight of a juvenoid and from about 0.5% to about 69.5% by weight of a chitin synthesis inhibitor, wherein the composition comprises up to 70% by weight of total active pesticides (e.g., juvenoid plus chitin synthesis inhibitor). For example, in one embodiment, the composition may comprise about 0.5% by weight of a juvenoid and about 69.5% by weight of a chitin synthesis inhibitor. In another embodiment, the composition may comprise about 69.5% by weight of a juvenoid and about 0.5% by weight of a chitin synthesis inhibitor. In yet another embodiment, the composition may comprise about 20% by weight of a juvenoid and about 50% by weight of a chitin synthesis inhibitor. In a further embodiment, the composition may comprise about 60% by weight of a juvenoid and about 10% by weight of a chitin synthesis inhibitor.

In an alternative embodiment, the amount of total active pesticide present in the composition may be less than 70%. For example, in one embodiment, the pesticide composition may comprise from about 0.5% to about 20% by weight of a juvenoid and from about 1% to about 30% by weight of a chitin synthesis inhibitor. In another embodiment, the pesticide composition may comprise from about 1% to about 3% by weight of a juvenoid and from about 1% to about 3% by weight of a chitin synthesis inhibitor. In an exemplary embodiment, the pesticide composition may comprise about 1.3% by weight of a juvenoid and about 1.3% by weight of a chitin synthesis inhibitor. One skilled in the art will understand that the embodiments of the present invention as described above are exemplary only and are not intended to be limiting.

Alternatively, the composition may optionally comprise one or more active pesticides (e.g., an adulticide) in addition to a juvenoid and a chitin synthesis inhibitor, at an amount such that the total of all active pesticides present in the composition does not exceed 70%.

The pesticide composition used to form the pesticide concentrates of the present invention may also include, in addition to the active pesticides discussed above, a combination of inert components or agents, such as surfactants, preservatives, solvents, antifoaming agents, thickeners, and the like.

The pesticide composition may include one or more surfactants, which may be of the emulsifying or wetting type, and may be selected from anionic, nonionic, amphoteric and zwitterionic surfactants and mixtures thereof. When the composition is to be combined with water, the use of at least one surfactant is generally required because the active pesticides are not water-soluble. In one embodiment, any surfactant known in the industry can be utilized. Examples of suitable anionic surfactants include, but are not limited to, alkyl sulfates, alkyl ether sulfates, alkaryl sulfonates, alkyl sulfosuccinates, n alkyl sarcosinates, alkyl phosphates, alkyl ether phosphates, alkyl ether carboxylates and alpha-olefin sulfonates, especially their ammonium, potassium, sodium, magnesium and mono, di and triethanolamine salts. Specific examples include dioctyl sodium sulphosuccinate (sold commercially as Aerosol® OT-B by Cytec) and ethoxylated tristyrylphenol phosphate potassium salt (sold commercially as Soprophor FLK by Rhodia).

Suitable amphoteric surfactants are those selected from the group consisting of sultaines (such as cocamidopropyl hydroxy sultaine); glycinates (such as cocoamphocarboxyglycinates); glycines (such as cocoamidopropyldimethylglycine); propionates (such as sodium lauriminodipropionate, sodium cocamphopropionate, disodium cocoamphodipropionate, and cocoamphocarboxypropionate). In addition, pseudo-amphoteric (ampholytic) surfactants such as betaines are also commonly grouped within the designation "Amphoteric" surfactants and can be used for similar purposes. Useful betaines include cocamidopropyl, coco, and oleamidopropyl.

Nonionic surfactants suitable for use in the composition of the invention may include condensation products of aliphatic ($C_8$-$C_{18}$) primary or secondary linear branched chain alcohols with alkylene oxides or phenols with alkylene oxides, usually ethylene oxide and generally having from 6 to 30 ethylene oxide groups. Suitable examples include the line of Tomadol® ethoxylates (Air Products), such as, for example, Tomadol® 23-5. Other nonionic surfactants suitable for use in the compositions of the present invention can include fatty acid alkanolamides. Representative fatty acid alkanolamides include those having $C_{10}$-$C_{18}$ carbons. For example, fatty acid diethanolamides such as isostearic acid diethanolamide and coconut fatty acid diethanolamide. Suitable fatty acid monoethanolamides, which may be used, include coconut fatty acid monoethanolamide and coco mono-isopropanolamide.

Semi-polar surfactants such as amine oxides are also suitable for use in the present invention. These include N-alkyl amine oxide and N-stearyl dimethylamine oxide. A suitable N-acyl amide oxide includes N-cocamidopropyl dimethylamine oxide. The hydrophobic portion of the amine oxide surfactant may be provided by a fatty hydrocarbon chain having from about 10-21 carbon atoms.

The pesticide composition may further comprise a thickener. A thickener is desired in order to keep the pesticides suspended within the composition. Examples of the thickener include water-soluble polymers such as water-soluble saccharide and water-soluble synthetic polymer and inorganic powder such as silica, magnesium silicate, aluminum silicate, magnesium aluminum silicate, bentonite, smectite, hectorite and aluminum oxide. A mixture of two or more kinds of the above-mentioned thickener is preferably used. Examples of the water-soluble saccharide include xanthan gum, gum arabic, rhamsan gum, locust bean gum, carrageenan, welan gum, ligninsulfonic acid, starch, and carboxymethylcellulose and its salt.

The pesticide composition of the present invention may further include an antifreezing agent selected from the group of alcohols, diols, polyols, and combinations thereof. Suitable examples of antifreezing agents that can be used in the present invention include glycerol, methanol, ethylene glycol, propylene glycol, potassium acetate, calcium magnesium acetate, sorbitol, or urea.

The pesticide composition of the present invention may further include an antifoam agent (such as Antifoam SE23 from Wacker Silicones Corp. or SAG 30 from Univar Corp.).

The pesticide composition of the present disclosure may also include one or more preservative compounds. The preservative compounds act to prevent corrosion of the container which holds the pesticide composition. Examples of suitable preservatives include, but are not limited to, sodium benzoate, benzoic acid, benzisothiazolinone (such as Proxel® GXL, produced by Arch Chemicals, Inc.) and potassium bicarbonate.

Preferably, the active pesticides are combined with one or more solvents (which may be, for example, water and/or an organic solvent) prior to forming the liquid pesticide concentrate for application to a locus or area. One of skill in the art will appreciate that the concentration of active pesticides contained in the pesticide composition will need to be adjusted as necessary to account for the form in which the composition is being formulated and to ensure the pesticide composition comprises the appropriate concentration of active pesticides as provided herein.

The pesticide composition as provided above is preferably dispersed in an aqueous medium (preferably water and/or an organic solvent) prior to its application to a locus or area where pest control is required, thereby forming a pesticide concentrate. In this respect, a pesticide concentrate is comprised of (1) a pesticide composition comprising active pesticides comprising from about 0.5% to about 69.5% by weight of a juvenoid and from about 0.5% to about 69.5% by weight of a chitin synthesis inhibitor, wherein the composition comprises up to 70% by weight of total active pesticide; and (2) an aqueous medium. All pesticide compositions that are or can be dispersed in an aqueous medium prior to application are, therefore, within the scope of the present invention (e.g. micro-emulsions, suspension concentrates, emulsifiable concentrates, wettable powders, water dispersible granules, capsule suspensions, emulsifiable granules, and combinations thereof). Preferably, the active pesticides are diluted in the pesticide concentrate to a concentration of from about 0.005% to about 0.5% by weight of the pesticide concentrate. In a preferred embodiment, the active pesticides are present in the pesticide concentrate at a concentration of from about 0.01% to about 0.1% by weight of the pesticide concentrate. One of skill in the art will appreciate that the weight of active pesticides added to the final product will need to be adjusted to account for the dilution and to ensure the final product comprises the appropriate final concentration of active pesticides.

The pesticide concentrate of the current invention can be prepared by dispersing the pesticide composition comprising the active pesticides in an aqueous medium to produce a pesticide concentrate suitable for application to a confined area where pest control is required. It should be understood that the current invention encompasses a variety of physical forms; however the concentrates of the present invention are generally directed to liquid solutions and suspensions. The concentrates of the present invention may be prepared by standard techniques known in the art. For instance, in one embodiment where the desired form is a liquid solution, the solution is prepared by first partially filling a container with an aqueous medium. Then, a pesticide composition comprising active pesticides comprising from about 0.5% to about 69.5% by weight of a juvenoid and from about 0.5% to about 69.5% by weight of a chitin synthesis inhibitor is combined with the aqueous medium, which may be water and/or an organic solvent. Generally an amount of from about 0.05 ounces to about 5 ounces of pesticide composition is added per gallon of aqueous medium. The container is then filled with a remaining amount of aqueous medium (e.g., water) in order to prepare the desired volume of solution. The mixture is agitated until the pesticide composition is fully dispersed within the aqueous medium, thereby forming a concentrated solution containing from about 0.005% to about 0.5% of the active pesticides.

In another embodiment, a pesticide carpet shampoo can be prepared by combining the pesticide composition disclosed herein with a carpet shampoo. The shampoo is diluted according to standard methods in the art, and then approximately 1 ounce of pesticide composition is added per gallon of diluted shampoo to be applied to an area. The shampoo is then mixed well in order to fully disperse the pesticide composition in the shampoo.

In yet another embodiment, a fogging solution can be prepared by combining the pesticide composition disclosed herein with an aqueous medium, such as water or petroleum distillates and mixing well until the composition is fully dispersed in the aqueous medium. The fogging solution is then used with fogging equipment as is known in the art, such as ultra-low volume (ULV) equipment, mechanical misting sprayers, aerosol generators, or thermal foggers.

In a further embodiment, a crop spray can be prepared by combining the pesticide composition disclosed herein with an aqueous medium, such as water or petroleum distillates and mixing well until the composition is fully dispersed in the aqueous medium. The crop spray is then used with crop spraying equipment as is known in the art, such as irrigation systems (for example, sprinkler, furrow, drip (trickle), or border irrigation systems), row crop sprayers, trailed crop sprayers, low volume mist blowers, hydraulic sprayers, compressed air sprayers, and the like.

Using methods known to those of skill in the art, the pesticide concentrates of the present invention are applied to a locus or a confined area (e.g., an interior surface location, an exterior location, or a perimeter of a structure) requiring pest control to treat and/or prevent pest infestation. The locus may comprise the interior of a residential dwelling, commercial building, transportation vehicle, warehouse, hospital, or other public building. The locus may further comprise void spaces, cracks, crevices, crawl spaces, hard-to-reach areas, basements, and the like. The locus may also comprise a spot treatment inside or about a structure which is susceptible to infestation or is infested. While compositions and methods of embodiments of the present disclosure are generally described with reference to interior application of the composition, it should be understood that the compositions may alternatively or in addition be applied to any exterior target surface such as landscaping materials, open ground space away from the structures, lawns, and the like.

In addition, the pesticide concentrates of the present invention may be applied to an open area (e.g., crop farm) containing crop products using methods known to those of skill in the art to control pests on crops. The crop products can be selected from any commonly known or used cash crops including fruits, vegetables, berries, nuts, leaves, seeds, grains and the like. Specific examples include crops, strawberries, raspberries, blueberries, melons, stone fruit, nut crops, potatoes, vegetables, turf grasses, seed crops (i.e., seed grasses, alfalfa seed), corn, rice, wheat, soybeans, dry beans, peanuts, cotton, sorghum, and other row crops, curcurbits, other small fruit crops, and horticultural plants.

Generally, the pesticide concentrates of the present invention are applied at a rate of from about 0.5 to about 3 gallons per from about 500 to 2,000 square feet of surface area to be treated. Preferably, the pesticide concentrates of the present invention are applied at a rate of about 1 gallon per 1,000 to 2,000 square feet of surface area to be treated.

A low-pressure broadcast spray may be used to apply the concentrate of the present invention to a confined area. Generally, when spraying, the concentrate is applied at the rate of from about 0.5 to about 3 gallons per at least 1,000 square feet of surface area.

A crop sprayer may be used to apply the concentrate of the present invention to crop products. Generally, when spraying crops, the concentrate is applied at the rate of up to about 20 gallons per acre.

The pesticide concentrates disclosed herein and the methods for controlling pests of the present disclosure are effective against a wide variety of pest populations generally. In several embodiments the pest is an arthropod and, in another embodiment, is an insect. The target pest may be selected from the group consisting of fleas, ants, cockroaches, beetles, earwigs, silverfish, crickets, spiders, centipedes, flies, midges, mosquitoes, gnats, moths, caterpillars, weevils, maggots, bedbugs, spiders, chiggers, cicadas, grasshoppers, root borers, stalk borers, vine borers, fruit borers, leafhoppers, fruitworms, mites, wasps, hornets, yellow jackets, bees, centipedes, millipedes, scorpions, pillbugs, sowbugs and the like. In a preferred embodiment, the pest is a cockroach, including brown banded cockroach, Asian cockroach, and German cockroach. In another preferred embodiment, the pest is a flea.

DEFINITIONS

As used herein, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study and can be readily appreciated by one of ordinary skill in the art.

As used herein, the term "w/w" designates the phrase "by weight and is used to describe the concentration of a particular substance in a mixture or solution.

As used herein, the term "treatment" or "treating" of a condition, such as pest infestation, includes inhibiting an existing condition or arresting its development; or ameliorating or causing regression of the condition. The term "preventing" or "prevention" of a condition, such as pest infestation, includes substantially blocking or inhibiting the development or growth of a condition before it starts. Compositions that treat or prevent infestations herein will preferably exhibit at least 90% efficacy.

As used herein, the term "pesticide" or "pesticidal" refers to a type of insecticide composition or mixture comprising a pesticide agent or agents and which is capable of preventing, reducing or eliminating pest infestations. Preferred pesticide agents of the present invention include juvenoids (such as pyriproxyfen or hydroprene) and chitin synthesis inhibitors (such as novaluron).

The following examples are intended to further illustrate and explain the present invention. The invention, therefore, should not be limited to any of the details in these examples.

Example 1—Method of Making a Pesticide Composition Comprising Novaluron and Pyriproxyfen A pesticide composition was prepared according to typical industry processing techniques using the active pesticides novaluron and pyriproxyfen as described hereinabove. Table 1 is the list of ingredients used to prepare a pesticide composition containing 1.30% pyriproxyfen and 1.3% novaluron.

TABLE 1

| Pesticide Composition | | |
| --- | --- | --- |
| Ingredient | Amount | Concentration |
| Pyriproxyfen | 13 lbs | 1.3% |
| Novaluron | 13 lbs | 1.3% |
| Tomadol 23-5 | 100 lbs | 10.0% |
| M-Pyrol | 200 lbs | 20.0% |
| Agnique ME 181-U | 674 lbs | 67.4% |
| TOTAL | 1000 lbs | 100% |

The pesticide composition was prepared by first adding the following ingredients to Tank 1 in the order provided:

200 lbs of M-Pyrol and 13 lbs of Novaluron. The contents of Tank 1 were mixed with moderate agitation for a minimum of 15 minutes until homogenous. 13 lbs of pyriproxyfen was added to Tank 1 with constant moderate agitation, and mixing continued until all of the pyriproxyfen was dissolved. Next, 674 lbs of Agnique ME 181-U was added to Tank 1 followed by the 100 lbs of Tomadol 23-5 under constant agitation and until the mixture was homogenous.

The product was examined for homogeneity and color, with the desired product being a transparent amber liquid with no inclusions.

Example 2—Method of Making a Pesticide Concentrate Comprising Novaluron and Pyriproxyfen A pesticide concentrate can be prepared using the pesticide composition set forth in Example 1.

Fill a container equipped with about one-quarter and one-third full of water. Add about 1 ounce of pesticide composition to the container per gallon of water. Add the remaining water. Agitate the mixture until the pesticide composition is completely dispersed in the water.

Example 3—Efficacy of Novaluron in Combination with Pyriproxyfen Applied to Selected Substrates Against German Cockroaches A study was initiated at Sierra Research Laboratories (Modesto, Calif.) to evaluate the efficacy of novaluron (CSI) in combination with pyriproxyfen (juvenoid) applied to selected substrates against German cockroaches.

Ceramic tile, vinyl tile, and unpainted plywood panels measuring 6"×6" were cleaned using soapy water to remove any residue left over from the manufacturing process and left to dry overnight. Six (6) L plastic storage boxes (Sterlite®) with lids were purchased from a local hardware store (Home Depot, Riverbank, Calif.) and cleaned as well and allowed to dry. Each substrate was treated with 0.95 mL of test material (1 gallon/1,000 ft$^2$ equivalent) prepared in accordance with Example 1 using a Pipetteman 1000, with the material being evenly distributed over the entire surface of the substrate using an acid brush. The material was allowed to dry and the substrates were placed into the plastic storage boxes, one per box. A 5 cm Petri dish was filled with dog food and a slice of orange for nourishment, and a water tube was added for moisture. The food dish was placed directly on the treated substrate to force exposure of the cockroaches. A 6" rolled piece of corrugated cardboard was placed in each replicate for harborage. A thin layer of petroleum jelly/mineral oil was applied to the rim to prevent escape.

Approximately forty (40) second and third instar nymphs were placed in each replicate and the lid was placed on top. Five replicates were prepared, one for each of the four treatments set forth in Table 2 and an untreated control. The test containers were placed in an IGR environmental chamber set at 80° F./80% RH and a 14:10 light/dark light cycle. The test was allowed to run for approximately two months to allow for adequate time for the cockroaches to go through their life cycle. Food and water was checked weekly and replaced as necessary.

An initial dose response/range finding bioassay was conducted with a combination of pyriproxyfen and novaluron to evaluate effective dosages for the tank mix. There were a high percentage of dead nymphs in all treated test groups (Table 2) with some adult cockroaches progressing to adult stage. Juvenoid effects (i.e., twisted wings) were noted in some of the adult cockroaches as well as some normal adults. The normal adults reproduced, but there appeared to be a dose and substrate relationship. Ceramic and vinyl tile showed the greatest IGR effects for the pyriproxyfen and novaluron combination at the test doses, with unpainted plywood proving to be the most severe substrate for these formations. The IGR combination demonstrated that the dual action of pyriproxyfen and novaluron prevented normal molting, metamorphosis, and reproduction at appropriate concentrations for selected substrates.

TABLE 2

Evaluation of Selected Pyriproxyfen/Novaluron Combinations Against German Cockroaches on Unpainted Plywood, Ceramic Tile, and Vinyl Tile

| Substrate | Treatment | Percent (%) of population (n = 5) | | | | % with reproduction (x/5) |
|---|---|---|---|---|---|---|
| | | Normal Nymphs | Dead Nymphs | Normal Adults | JH Adults | |
| Unpainted Plywood | Untreated Control | 0 | 22.4 | 77.6 | 0 | 100 |
| | 0.01% Pyriproxyfen + 0.005% Novaluron | 3.0 | 47.0 | 46.5 | 3.5 | 100 |
| | 0.01% Pyriproxyfen + 0.01% Novaluron | 0.4 | 40.8 | 56.1 | 2.6 | 100 |
| | 0.02% Pyriproxyfen + 0.02% Novaluron | 0 | 86.8 | 9.5 | 3.7 | 40.0 |
| | 0.03% Pyriproxyfen + 0.02% Novaluron | 0.0 | 92.7 | 3.1 | 4.2 | 20.0 |
| Ceramic Tile | Untreated Control | 0 | 9.4 | 90.6 | 0 | 100 |
| | 0.01% Pyriproxyfen + 0.005% Novaluron | 1.2 | 83.1 | 6.0 | 9.6 | 40.0 |
| | 0.01% Pyriproxyfen + 0.01% Novaluron | 0.6 | 92.8 | 1.7 | 5.0 | 20.0 |
| | 0.02% Pyriproxyfen + 0.02% Novaluron | 0 | 98.9 | 0 | 1.1 | 0 |
| | 0.03% Pyriproxyfen + 0.02% Novaluron | 0 | 97.5 | 0 | 2.5 | 0 |

TABLE 2-continued

Evaluation of Selected Pyriproxyfen/Novaluron Combinations Against
German Cockroaches on Unpainted Plywood, Ceramic Tile, and Vinyl Tile

| | | Percent (%) of population (n = 5) | | | | % with |
|---|---|---|---|---|---|---|
| Substrate | Treatment | Normal Nymphs | Dead Nymphs | Normal Adults | JH Adults | reproduction (x/5) |
| Vinyl Tile | Untreated Control | 0 | 11.7 | 88.3 | 0 | 100 |
| | 0.01% Pyriproxyfen + 0.005% Novaluron | 0.5 | 67.5 | 7.8 | 24.3 | 20.0 |
| | 0.01% Pyriproxyfen + 0.01% Novaluron | 0 | 86.1 | 1.2 | 12.7 | 0 |
| | 0.02% Pyriproxyfen + 0.02% Novaluron | 0 | 95.7 | 0 | 4.3 | 0 |
| | 0.03% Pyriproxyfen + 0.02% Novaluron | 0 | 96.8 | 0 | 3.2 | 0 |

Definitions:
Normal Nymph—Nymph that has normal appearance that was alive at time of evaluation (initial infestation)
Dead Nymph—Nymph that died sometime during the test either from natural or JH affects (initial infestation)
Normal Adult—Adult that molted normally and has no JH affect
JH Adult—Juvenile Hormone affected adult, molted but has darkened cuticle and/or crinkled wings/wingpads A second series of evaluations was designed to evaluate the pyriproxyfen and novaluron alone and in combination. Preliminary results from the second evaluation showed molting abnormalities of mid-instar cockroaches on all three substrates in novaluron-only test groups and the combination novaluron/pyriproxyfen test groups. These cockroaches were dead prior to molt or in a few cases during the molt and comprised <50% of the test populations. Morphological characteristics of juvenoid activity were observed in the pyriproxyfen-only test groups and pyriproxyfen/novaluron test group. These effects were most notably twisted wings and darkened cuticle with individuals alive in these treatment groups. The untreated control groups showed normal molting and metamorphosis to the adult stage with some females producing ootheca (egg capsules).

Example 4—Efficacy of Novaluron in Combination with Pyriproxyfen Applied to Selected Substrates Against *Ctenocephalides Felis* (Cat Flea)

Sand/Media Bioassay

Seventy-five (75) grams of sifted sand was added to 25 grams of flea media (dry blood/dog food mix) and mixed thoroughly in an eight (8) ounce deli squat cup. Five (5) mL of diluted test material (prepared in accordance with Example 1) was added to the mixture and mixed thoroughly. Each mixture was allowed to dry completely overnight. Fifteen (15) grams of the mixture was added to a one (1) ounce soufflé cup and approximately 20 one-day old flea eggs were added to the top of the mixture. Five replicates were prepared, one for each of the four treatments set forth in Table 3 and an untreated control. Lids with pin holes were placed onto each cup and placed into an environmental chamber set at 80° F./80% RH. The bioassay was scored for adult emergence approximately four weeks later.

Carpet Bioassay

Samples of a medium length synthetic carpet were cut into 3.5" circles and vacuumed with a suction type vacuum prior to treatment. A 100 ft² treatment area was measured out on gravel and five carpet samples were placed randomly within the area on paper to prevent contamination. Approximately 252.3 mL of diluted test material (prepared in accordance with Example 1) was sprayed evenly across the entire treatment areas using a 1 gallon compressed air sprayer (B&G Equipment Co.) with a fan nozzle. The carpet was picked up immediately after treatment and the test material rubbed into the carpet fibers with a gloved hand. This method was repeated for all treatment groups. Each sample was allowed to dry completely then was placed into an 8-ounce deli squat cup. Approximately 0.25 teaspoon of flea media and 0.25 teaspoon of sand was added to each sample and rubbed into the fibers.

Approximately 100 one-day old cat flea eggs were deposited on top of each carpet after being separated under a microscope. A lid with fine mesh organdy was placed on each cup and all replicates were placed into an environmental chamber set at 80° F./80% RH. The bioassay was scored for adult emergence approximately four weeks later.

The results of both the sand/media and carpet bioassays are set forth in Table 3.

TABLE 3

Evaluation of Selected Pyriproxyfen/Novaluron Combinations Against
*Ctenocephalides felis* on Sand/Media and Carpet Substrates

| | Trial 2 % Adult Emergence | |
|---|---|---|
| Treatment | Sand/Media 1 gal/1,500 ft² | Carpet 1 gal/1,500 ft² |
| Untreated Control | 57.0 | 54.8 |
| 0.01% pyriproxyfen + 0.01% novaluron | 0 | 4.2 |
| 0.01% pyriproxyfen + 0.03% novaluron | 0 | 0 |
| 0.01% pyriproxyfen + 0.05% novaluron | 0 | 0 |
| 0.01% pyriproxyfen + 0.10% novaluron | 0 | 0 |

Example 5—Individual Dose Response for Novaluron and Pyriproxyfen Products in Sand/Media Against *Ctenocephalides felis* (Cat Flea)

The test substances set forth in Table 4 were obtained from LABServices:

TABLE 4

Test Substances

| Insecticide | Brand | EPA Reg. No. | Container No. | Lot No. |
|---|---|---|---|---|
| 10% Novaluron | Pedestal ® | 66222-40-400 | 1145-178 | 00113249 |
| 103 grams Novaluron/liter | Rimon ® Supra | N/A | 1145-179 | 00116017 |
| 0.83 lb Novaluron/gallon | Rimon ® 0.83EC Insecticide | 66222-35-400 | 1145-180 | BO0075020 |
| 10.00% 2-[1-Methyl-2-(4-phenoxyphenoxy)ethoxy] pyridine (Pyriproxyfen) | NyGuard ™ IGR Concentrate | 1021-1603 | N/A | AA61 |

Seventy-five (75) grams of sifted sand was added to 25 grams of flea media (dry blood/dog food mix) and mixed thoroughly in an eight (8) ounce deli squat cup. Five (5) mL of diluted test material was added to the mixture and mixed thoroughly. Each mixture was allowed to dry completely overnight. 15 grams of the mixture was added to a one (1) ounce soufflé cup and approximately 20 one-day old flea eggs were added to the top of the mixture. Five replicates were prepared, one for each of the four treatments set forth in Table 5 and a control (water). Lids with pin holes were placed onto each cup and placed into an environmental chamber set at 80° F./80% RH. The bioassay was scored for adult emergence approximately four weeks later.

TABLE 5

Evaluation of Selected Pyriproxyfen and Novaluron Pesticides Individually Against *Ctenocephalides felis* on Sand/Media

| Treatment (% a.i.) | % Adult Emergence |
|---|---|
| $H_2O$ $\alpha^2$ | 60.0% |
| $H_2O$ $\alpha^1$ | 45.0% |
| 0.000005% Rimon 0.83EC | 46.0% |
| 0.00005% Rimon 0.83EC | 27.0% |
| 0.0005% Rimon 0.83EC$^2$ | 0.0% |
| 0.0005% Rimon 0.83EC$^1$ | 0.0% |
| 0.005% Rimon 0.83EC | 0.0% |
| 0.05% Rimon 0.83EC | 0.0% |
| 0.000005% Rimon Supra | 48.0% |
| 0.00005% Rimon Supra | 41.0% |
| 0.0005% Rimon Supra$^2$ | 0.0% |
| 0.0005% Rimon Supra$^1$ | 0.0% |
| 0.005% Rimon Supra | 0.0% |
| 0.05% Rimon Supra | 0.0% |
| 0.000005% Pedestal | 41.0% |
| 0.00005% Pedestal | 28.0% |
| 0.0005% Pedestal$^2$ | 0.0% |
| 0.0005% Pedestal$^1$ | 0.0% |
| 0.005% Pedestal | 0.0% |
| 0.05% Pedestal | 0.0% |
| 0.000001% NyGuard IGR | 40.0% |
| 0.00001% NyGuard IGR | 43.0% |
| 0.0001% NyGuard IGR$^2$ | 4.0% |
| 0.0001% NyGuard IGR$^1$ | 0.0% |
| 0.001% NyGuard IGR | 0.0% |
| 0.01% NyGuard IGR | 0.0% |

$^{1/2}$Repeated Same Rate

Although the invention described herein is susceptible to various modifications and alternative iterations, specific embodiments thereof have been described in greater detail above. It should be understood, however, that the detailed description of the pesticide composition is not intended to limit the invention to the specific embodiments disclosed. Rather, it should be understood that the invention is intended to cover all modifications, equivalents, and alternatives falling within the spirit and scope of the invention as defined by the claim language.

What is claimed is:

1. A method for controlling cockroaches and fleas in a confined area, which method comprises applying to the confined area a pesticide concentrate comprising: (1) a pesticide composition comprising a juvenoid selected from the group consisting of epofenonane, hydroprene, kinoprene, methoprene, pyriproxyfen, triprene, and combinations thereof; and a chitin synthesis inhibitor selected from the group consisting of bistrifluron, buprofezin, chlorfluazuron, cyromazine, flucycloxuron, hexaflumuron, lufenuron, novaluron, penfluron, teflubenzuron, triflumuron, and combinations thereof; and (2) an aqueous medium, wherein the pesticide composition is dispersed in the aqueous medium to form the pesticide concentrate comprising from about 0.005% to about 0.5% by weight of the juvenoid and the chitin synthesis inhibitor.

2. The method of claim 1 wherein the pesticide concentrate is applied in an amount of about 0.5 to about 3 gallons per about 500 to 2,000 square feet of confined area.

3. A method for protecting a confined area from fleas, cockroaches, ants, crickets, beetles, flying pests and moths infestation and/or treating a confined area having an infestation of cockroaches, ants, crickets, beetles, flying pests and moths to substantially eliminate the infestation, which method comprises:
   a. identifying a confined area; and
   b. applying a pesticide concentrate to the confined area or interior surface, the pesticide concentrate comprising (1) a pesticide composition comprising juvenoid selected from the group consisting of epofenonane, hydroprene, kinoprene, methoprene, pyriproxyfen, triprene, and combinations thereof; and a chitin synthesis inhibitor selected from the group consisting of bistrifluron, buprofezin, chlorfluazuron, cyromazine, flucycloxuron, hexaflumuron, lufenuron, novaluron, penfluron, teflubenzuron, triflumuron, and combinations thereof; and (2) an aqueous medium, wherein the pesticide composition is dispersed in the aqueous medium to form the pesticide concentrate comprising from about 0.005% to about 0.5% by weight of the juvenoid and the chitin synthesis inhibitor.

4. The method of claim 3, wherein the confined area is selected from a group comprising of an interior surface, interior area, exterior area, a structure, a perimeter of a structure, a food or non-food warehouse, and a food-handling establishment.

5. The method of claim 3, wherein the beetles are selected from the group consisting of red flour beetles, confused flour beetles, merchant grain beetles, saw-toothed grain beetles, warehouse beetles, cigarette beetles, and dermisted beetles, the flying pests are selected from the group comprising flies, mosquitoes, gnats, midges and the moths are selected from the group consisting of meal moths, rice moths, and tobacco moths; lesser grain borers.

6. The method of claim 3, wherein the pesticide concentrate is applied in an amount of about 0.5 to about 3 gallons per about 500 to 2,000 square feet of confined area.

7. The method of claim 3, wherein the pesticide concentrate further comprises an adulticide insecticide.

8. The method of claim 3, wherein the pesticide concentrate is applied by spot treating the identified location.

9. The method of claim 3, wherein:
(a) the confined area is a structure and the perimeter of the structure comprises an area from about 1 to about 10 feet adjacent to all sides of the structure, and/or
(b) the pesticide concentrate is applied at a height of from about 1 to about 5 feet from the foundation of the structure.

10. The method of claim 1, wherein the chitin synthesis inhibitor is novaluron and the juvenoid is pyriproxyfen.

11. The method of claim 3, wherein the chitin synthesis inhibitor is novaluron and the juvenoid is pyriproxyfen.

12. The method of claim 1, further controlling ants.

13. The method of claim 2, wherein the chitin synthesis inhibitor is novaluron and the juvenoid is pyriproxyfen.

14. The method of claim 6, wherein the chitin synthesis inhibitor is novaluron and the juvenoid is pyriproxyfen.

15. The method of claim 1, wherein the pesticide concentrate comprises from about 0.01% to about 0.1% by weight of the juvenoid and the chitin synthesis inhibitor.

16. The method of claim 3, wherein the pesticide concentrate comprises from about 0.01% to about 0.1% by weight of the juvenoid and the chitin synthesis inhibitor.

17. The method of claim 1, wherein pesticide concentrate comprises from about 0.0025% to about 0.25% by weight of the juvenoid and from about 0.0025% to about 0.25% by weight the chitin synthesis inhibitor.

18. The method of claim 3, wherein the pesticide concentrate comprising from about 0.0025% to about 0.25% by weight of the juvenoid and from about 0.0025% to about 0.25% by weight the chitin synthesis inhibitor.

19. The method of claim 15, wherein the pesticide concentrate comprises from about 0.005% to about 0.05% by weight of the juvenoid and from about 0.005% to about 0.05% by weight the chitin synthesis inhibitor.

20. The method of claim 16, wherein the pesticide concentrate comprises from about 0.005% to about 0.05% by weight of the juvenoid and from about 0.005% to about 0.05% by weight of the chitin synthesis inhibitor.

* * * * *